US006254856B1

(12) United States Patent
Tsuchiya

(10) Patent No.: US 6,254,856 B1
(45) Date of Patent: Jul. 3, 2001

(54) COMPOSITIONS FOR THE REMOVAL OF DENTAL PLAQUE

(75) Inventor: Rie Tsuchiya, Birkerød (DK)

(73) Assignee: Novo Nordisk, A/S, Bagsvaerd (DK)

( * ) Notice: Subject to any disclaimer, the term of this patent is extended or adjusted under 35 U.S.C. 154(b) by 0 days.

(21) Appl. No.: 09/165,183

(22) Filed: Oct. 2, 1998

(30) Foreign Application Priority Data

Apr. 16, 1996 (DK) .................................................... 0444/96

(51) Int. Cl.[7] ...................................................... A61K 7/16
(52) U.S. Cl. ............................................ 424/49; 435/211
(58) Field of Search ............................. 424/49; 435/183, 435/211

(56) References Cited

U.S. PATENT DOCUMENTS

| 4,353,891 | * | 10/1982 | Guggenheim et al. | ................. | 424/50 |
| 4,438,093 | | 3/1984 | Shimada et al. | ........................ | 424/50 |
| 4,466,954 | * | 8/1984 | Ichikawa et al. | ....................... | 424/50 |
| 5,145,665 | | 9/1992 | Klueppel et al. | ....................... | 424/50 |
| 5,320,830 | * | 6/1994 | Lukcovic et al. | ....................... | 424/52 |
| 5,637,491 | * | 6/1997 | Campana et al. | ..................... | 435/211 |
| 5,853,702 | * | 12/1998 | Berka et al. | ............................ | 424/50 |

FOREIGN PATENT DOCUMENTS

| 0 195 672 | | 9/1986 | (EP) . |
| 2 651 433 | | 3/1991 | (FR) . |
| 2 206 585 | | 1/1989 | (GB) . |
| 47-34148 | * | 8/1972 | (JP) . |
| 94055662 | * | 5/1998 | (JP) . |
| WO 98/00528 | * | 1/1998 | (WO) . |
| WO 98/00529 | * | 1/1998 | (WO) . |
| WO 98/18437 | * | 5/1998 | (WO) . |

OTHER PUBLICATIONS

Sun J. The In Vitro Effects of Dextranase on Dental Plaque Produced by Streptococcus Mutans. Acta Microbiol Sin 28(3)242–248, 1988.*
Dialog Information Services, File 5, BIOSIS, Dialog Accession No. 7107517, Sun et al. (1998) Acta Microbiologica Sinica 28(3) :242–248.
File WPI, Derwent Accession No. 72–56480, Kojin Co. Ltd.
Dialog Information Services, File 351, WPI, Dialog Accession No. 004561593.
Dialog Information Services, File 155, Medline, Dialog Accession No. 02909591.
Budtz–Jørgensen et al. (1977), Scand. J. Dent. Res. 85:209–215.
Guggenheim et al. (1972), Caries Res. 6:289–297.

* cited by examiner

Primary Examiner—Ralph Gitomer
(74) Attorney, Agent, or Firm—Elias J. Lambiris

(57) ABSTRACT

The present invention relates to oral care compositions and products comprising a dextranase and a mutanase, and optionally other enzymes.

5 Claims, 3 Drawing Sheets

COMPOSITIONS FOR THE REMOVAL OF DENTAL PLAQUE

CROSS-REFERENCE TO RELATED APPLICATIONS

This application is a continuation of PCT/DK97/00162 filed Apr. 16, 1997 and claims priority under 35 U.S.C. 119 of Danish application 0444/96 filed Apr. 16, 1996, the contents of which are fully incorporated herein by reference.

FIELD OF THE INVENTION

The present invention relates to oral care compositions and products comprising a dextranase arid a mutanase, and optionally other enzymes.

The invention also relates to the use of the composition and product of the invention for the removal of dental plaque and preventing the formation of dental plaque.

BACKGROUND OF THE INVENTION

The formation of dental plaque leads to dental caries, gingival inflammation, periodontal disease, and eventually tooth loss. Dental plaque is a mixture of bacteria, epithelial cells, leukocytes, macrophages, and other oral exudate. Said bacteria produce highly branched polysaccharides which together with microorganisms from the oral cavity form an adhesive matrix for the continued proliferation of plaque.

As plaque continues to accumulate rock hard white or yellowish deposits arise. These deposits are called calcified plaque, calculus or tartar, and are formed in the saliva from plaque and minerals, such as in particular calcium.

Oral Polysaccharides

Oral polysaccharides are produced from sucrose introduced into the mouth, e.g. as a food or beverage constituent, by the action of cariogenic microorganisms, such as *Streptococcus mutans* or *Streptococcus sanguis*, growing in the oral cavity.

Said oral polysaccharides comprise water-soluble dextran, having large portions of α-1,6 glucosidic linkage, and a major component of water-insoluble extracellular polysaccharides called "mutan" comprised of a backbone with α-1,3-glycosidic linkages aid branches with α-1,6-glycosidic linkages.

Mutan bind to hydroxyapatite (constituting the hard outer porous layer of the teeth) and to acceptor proteins on the cell surface of said cariogenic bacteria adhering to the teeth surface.

Mutanase

Mutanases are α-1,3-glucanases (also known as α-1,3-glucanohydrolases) which degrade the α-1,3-glycosidic linkages in mutan. Mutanases have been described derived from Trichoderma (Hasegawa et al., (1969), Journal of Biological Chemistry 244, p. 5460–5470; Guggenheim and Haller, (1972), Journal of Dental Research 51, p. 394–402) and from a strain of Streptomyces (Takehara et al., (1981), Journal of Bacteriology 145, p. 729–735), *Cladosporium resinae* (Hare et al. (1978), Carbohydrate Research 66, p. 245–264), Pseudomonas sp. (U.S. Pat. No. 4,438,093), Flavobacterium sp. (JP 77038113), *Bacillus circulanse* (JP 63301738) and Aspergillus sp. A mutanase gene from *Trichoderma harzianum* has been cloned and sequenced (Japanese Patent No. 4-58889/A).

Dextranase

Dextranases are α-1,6-glucanases (also known as 1,6-α-D-glucan 6 glucanohydrolases) which degrade the α-1,6-glycosidic linkages in dextran. Several microorganisms are capable of producing dextranases, among them fungi of genera Penicillium, Paecilomyces, Aspergillus, Fusarium, Spicaria, Verticillium, Helminthosporium and Chaetomium; bacteria of the genera Lactobacillus, Streptococcus, Cellvibrio, Cytophaga, Brevibacterium, Pseudomonas, Corynebacterium, Arthrobacter and Flavobacterium and yeasts such as *Lipomyces starkeyi*.

Commercially available products include Dextranase 50 L from Novo Nordisk A/S produced by fermentation of strains of *Penicillium lilacium*. Dextranase 50 L is used in the sugar industry to break down dextran in raw sugar juice or syrup.

To be able to sufficiently guarantee the capability of chewing, e.g. foods, during a whole lifetime it is necessary to keep the teeth in a good condition and to obtain a good oral hygiene. This can be obtained by brushing the teeth frequently using toothpaste or the like. The mouth may further advantageously be rinsed with a mouth wash comprising anti-microbial agents.

To prevent the formation of dental caries, plaque, and tartar, it has been suggested to add a dextranase and/or a mutanase and/or other enzymes to oral care compositions and products.

U.S. Pat. No. 4,353,891 (Guggenheim et al.) concerns plaque removal using mutanase from *Trichoderma harzianum* CBS 243.71 to degrade mutan synthesized by cultivating *Streptococcus mutans* strain CBS 350.71 identifiable as OMZ 176. It is stated that the critical ingredient in dental plaque is water-insoluble polysaccharide with α-1,3-glucosidic bonds and that such polysaccharide material termed mutan is not attacked by dextranase.

Guggenheim et al., (1972), Caries Res. 6, p. 289–297) discloses that the extent of the dental plaque of rats is not significantly affected by the simultaneous use of a dextranase and a 1,3-glucanase (mutanase).

Hare et al. (1978), Carbohydrate Research 66, p. 245–264, found that a synergistic effect is obtained when hydrolysing and solubilizing oral glucans with a bacterial dextranase in combination with bacterial α-1,3 glucanase from *Cladosporium resinae*.

U.S. Pat. No. 4,438,093 (The Research Foundation for Microbial diseases of Osaka) describes oral compositions comprising a dextranase and a α-1,3-glucanase (mutanase), both being present in an amount of 0.5 to 100 enzyme units per gram of said oral composition, in an enzyme unit ratio of 1:2 to 2:1. Said dextranase is derived from a bacteria within the genus Corynbacterium and said α-1,3-glucanase is derived from a bacteria-within the genus Pseudomonas.

GB 2,206,585 (Dental Chem Co LTD) described a teeth cleaning agent containing hydroxyapatite as polishing agent, with a laevanase, dextranase and mutanase immobilized on the hydroxyapatite.

U.S. Pat. No. 5,145,665 (Henkel) discloses a composition for the care of the mount and teeth comprising a dextranase and/or a 1,3-glucanase for cleaving polysaccharides in the mouth.

FR 2,651,433 (DANA) concerns dentifrice products containing a dextranase to acts on recent plaque, a mutanase to acts on old and insoluble plaque, and a mixture or other enzymes having bactericide action.

U.S. Pat. No. 5,320,830 (Proctor & Gamble) describes toothpaste compositions for the reduction of plaque and gingivitis comprising a) a surfactant, b) an enzyme, c) chelating agent d) a fluoride source, e) a silica abrasive and d) a carrier. The enzyme is an endoglucanase, papain, a dextranase and/or a mutanase.

SUMMARY OF THE INVENTION

It is the object of the present invention to provide oral care products which safely (i.e. without harming the tissue and structure of the oral cavity) and effectively prevent the formation of dental plaque and/or removes already deposited dental plaque.

In the first aspect the invention relates to an oral care composition comprising a *Paecilomyces lilacinum* dextranase and a mutanase. Further the invention relates to oral care products thereof, such as a dentifrice. Finally the invention relates to the use of a composition or product of the invention for preventing the formation of dental plaque or removing dental plaque.

DETAILED DESCRIPTION OF THE INVENTION

Figure 1:
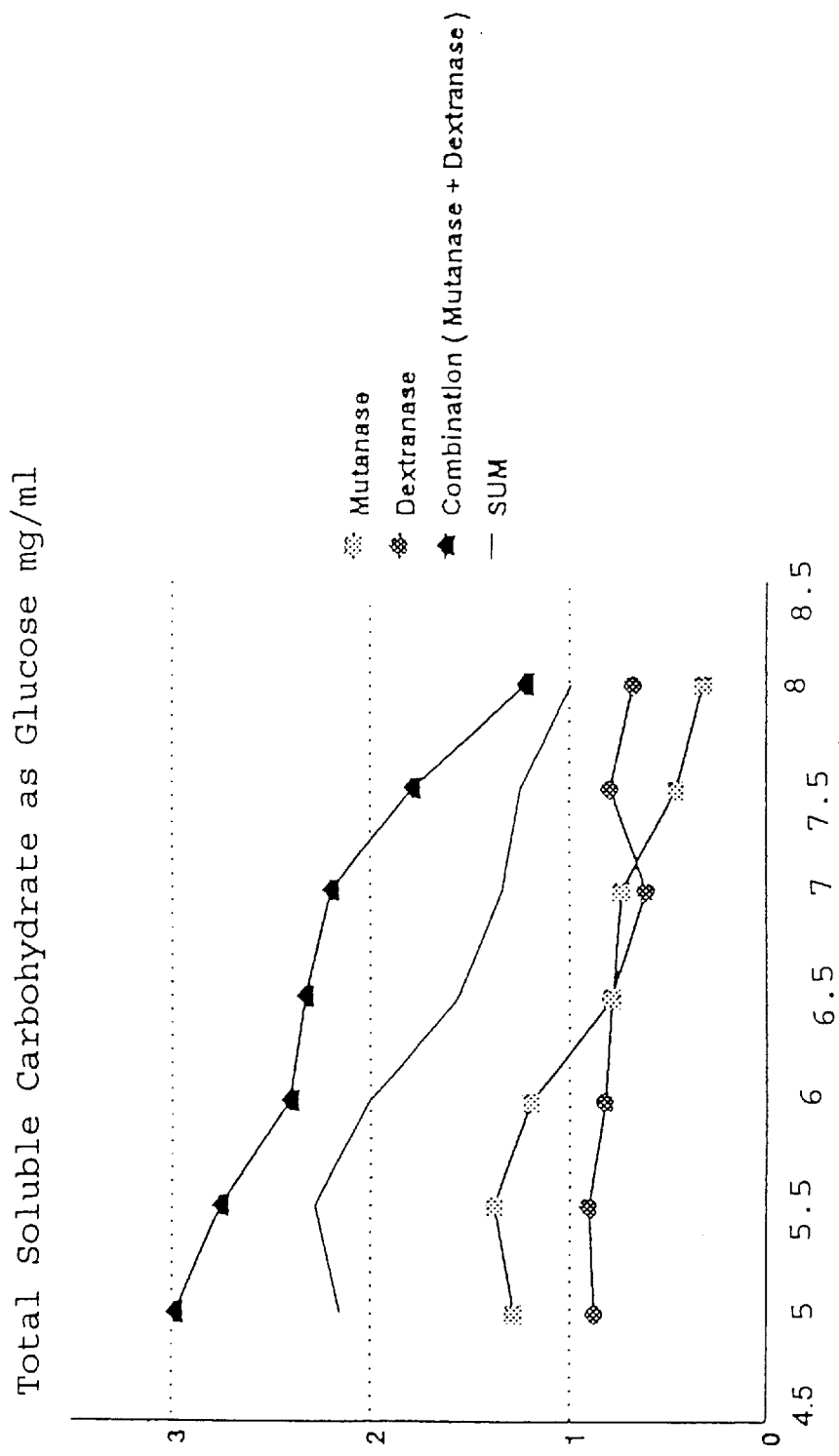
FIG. 1 shows hydrolysis of mutan with *Paecilomyces lilacinum* dextranase and/or *Trichoderma harzianum* mutanase within the pH range from 5.0 to 8.0.

All patents, patent applications, and literature references referred to herein are hereby incorporated by reference in their entirety.

It is the object of the present invention to provide oral care products which safely (i.e. without harming the tissue and structure of the oral cavity) and effectively prevent the formation of dental plague and/or removes already deposited dental plaque.

It is to be understood that said oral care products directly or indirectly may also have other oral care functions at the same time, e.g. prevention of dental holes or gingivitis.

All concerned oral care compositions and products prepared there from referred to in the present application comprise enzymes and have a pH in the range from 6.0 to about 8.0, which is the pH of most oral care products.

The present inventors have found that a synergistic effect is obtained when using specific dextranases and mutanases in oral care products.

Oral Care Compositions

Accordingly, the first object of the invention is to provide an oral care composition comprising a dextranase derived from *Paecilomyces lilacinum* and a mutanase.

The reduced amount of enzyme needed is of commercial interests; for oral care product manufactures as the cost of producing such product according to the invention can be reduced. Further, if the original amount of enzymes are added to the product an improved product can be obtained. Also the user of an oral care product of the invention (which will be describe in more details below), prepared from the oral care composition of the invention, will benefit from the present invention, as the direct and indirect disadvantages (e.g. yellow deposits on the teeth and prevention of dental holes and gingivitis, respectively) can be prevented safely and more effectively than with prior art products.

A mutanase suitable for the use in combination with a mutanase in an oral care composition of the invention may be produced by filamentous fungi from the group including Trichoderma, in particular from a strain of *Trichoderma harzianum*, such as *Trichoderma harzianum* CBS 243.71, or Penicillium, in particular a strain of *Penicillium funiculosum*, such as *Penicillium funiculosum* NRRL 1768, or a strain of *Penicillium lilacinum*, such as *Penicillium lilacinum* NRRL 896, or a strain of Penicillium purpurogenum, such as the strain of *Penicillium purpurogenum* CBS 238.95, or a strain of the genus Pseudomonas, or a strain of Flavobacterium sp., or a strain of *Bacillus circulanse* or a strain of Aspergillus sp., or a strain of Streptomyces.

The mutanase may also be derived from *Penicillium purpurogenum*.

U.S. Pat. No. 4,353,981 (Guggenheim et al.) discloses the use of the *Trichoderma harzianum* CBS 243.71 mutanase, the *Penicillium funiculosum* NRRL 1768 mutanase and the *Penicillium lilacinum* NRRL 896 mutanase for the removal of dental plaque.

Reference to the other above mentioned mutanases can found above in the background of the invention section.

An oral care composition of the invention may suitably comprise an amount of *Paecilomyces lilacinum* dextranase and a mutanase equivalent to an enzyme activity, calculated as enzyme activity units in the final oral care product, in the range from 0.001 KDU to 1000 KDU/ml, preferably from 0.01 KDU/ml to 500 KDU/ml, especially from 0.1 KDU/ml to 100 KDU/ml, and from 0.001 MU/ml to 1000 MU/ml, preferably from 0.01 MU/ml to 500 MU/ml, especially from 0.01 MU/ml to 100 MU/ml and from 0.01 MU/ml to 100 Mu/ml, respectively.

The present inventors have surprisingly found that when combining a dextranase from *Paecilomyces lilacinum* and a mutanase from *Trichoderma harzianum* a synergistic effect is obtained when removing plaque in a in vitro assay at pH 7.0 (see Example 2).

In a preferred embodiment the mutanase used is recombinant.

It is necessary that the enzymes (i.e. dextranase and the mutanase) are substantially active at temperatures between 20° C. and 45° C., especially around 37° C., as the temperature prevailing in the human mouth lies within said temperature interval.

The term "substantially active" means in the context of the present invention that the enzyme in question has a relative activity above 70s, in particular above 80%, especially above 90% of the activity at the temperature optimum.

It is also contemplated according to the invention to include other enzyme activities in the oral care compositions of the invention. Contemplated enzymes, beside dextranase and mutanase, may be from the group including proteases, such as papain, endoglucosidases, lipases, amylases and mixtures thereof.

Oral Care Products

The invention also relates to oral care products comprising an oral care composition of the invention. The oral care product may have any suitable physical form (i.e. powder, paste, gel, liquid, ointment, tablet etc.). An "oral care product" can be defined as a product which can be used for maintaining or improving the oral hygiene in the mouth of humans and animals, by preventing formation of dental plaque, removing dental plaque, preventing and/or treating dental diseases etc.

At least in the context of the present invention oral care products do also encompass products for cleaning dentures, artificial teeth and the like.

Examples of such oral care products include toothpaste, dental cream, gel or tooth powder, odontic, mouth washes, pre- or post brushing rinse formulations, chewing gum, lozenges, and candy.

Toothpastes and tooth gels typically include abrasive polishing materials, foaming agents, flavouring agents, humectants, binders, thickeners, sweetening agents, whitening/bleaching/stain removing agents, water, and optionally enzymes.

Mouth washes, including plaque removing liquids, typically comprise a water/alcohol solution, flavour, humectant, sweetener, foaming agent, colorant, and optionally enzymes.

Abrasives

Abrasive polishing material might also be incorporated into the dentifrice product of the invention. According to the invention said abrasive polishing material includes alumina and hydrates thereof, such as alpha alumina trihydrate, magnesium trisilicate, magnesium carbonate, kaolin, aluminosilicates, such as calcined aluminum silicate and aluminum silicate, calcium carbonate, zirconium silicate, and also powdered plastics, such as polyvinyl chloride, polyamides, polymethyl methacrylate, polystyrene, phenol-formaldehyde resins, melamine-formaldehyde resins, urea-formaldehyde resins, epoxy resins, powdered polyethylene, silica xerogels, hydrogels and aerogels and the like. Also suitable as abrasive agents are calcium pyrophosphate, water-insoluble alkali metaphosphates, dicalcium phosphate and/or its dihydrate, dicalcium orthophosphate, tricalcium phosphate, particulate hydroxyapatite and the like. It is also possible to employ mixtures of these substances.

Dependent on the oral care product the abrasive product may be present in from 0 to 70 by weight, preferably from 1% to 70%. For toothpastes the abrasive material content typically lies in the range of from 10% to 70% by weight of the final toothpaste product.

Humectants are employed to prevent loss of water from e.g.

toothpastes. Suitable humectants for use in oral care products according to the invention include the following compounds and mixtures thereof: glycerol, polyol, sorbitol, polyethylene glycols (PEG), propylene glycol, 1,3-propanediol, 1,4-butanediol, hydrogenated partially hydrolysed polysaccharides and the like. Humectants are in general present in from 0% to 80%, preferably 5 to 70% by weight in toothpaste.

Silica, starch, tragacanth gum, xanthan gum, extracts of Irish moss, alginates, pectin, cellulose derivatives, such as hydroxyethyl cellulose, sodium carboxymethyl cellulose and hydroxypropyl cellulose, polyacrylic acid and its salts, polyvinylpyrrolidone, can be mentioned as examples of suitable thickeners and binders, which helps stabilizing the dentifrice product. Thickeners may be present in toothpaste creams and gels in an amount of from 0.1 to 20% by weight, and binders to the extent of from 0.01 to 10% by weight of the final product.

Foaming Agents

As foaming agent soap, anionic, cationic, non-ionic, amphoteric and/or zwitterionic surfactants can be used. These may be present at levels of from 0% to 15%, preferably from 0.1 to 13%, more preferably from 0.25 to 10% by weight of the final product.

Surfactants

Surfactants are only suitable to the extent that they do not exert an inactivation effect on the present enzymes. Surfactants include fatty alcohol sulphates, salts of sulphonated mono-glycerides or fatty acids having 10 to 20 carbon atoms, fatty acid-albumen condensation products, salts of fatty acids amides and taurines and/or salts of fatty acid esters of isethionic acid.

Sweetening Agents

Suitable sweeteners include saccharin.

Flavoring Agents

Flavours, such as spearmint, are usually present in low amounts, such as from 0.01% to about 5% by weight, especially from 0.1% to 5%.

Whitening/bleaching Agents

Whitening/bleaching agents include $H_2O_2$ and may be added in amounts less that 5% preferably from 0.25 to 4%, calculated on the basis of the weight of the final product.

Water

Water is usually added in an amount giving e.g. toothpaste a flowable form.

Additional agents

Further water-soluble anti-bacterial agents, such as chlorhexidine digluconate, hexetidine, alexidine, quaternary ammonium anti-bacterial compounds and water-soluble sources of certain metal ions such as zinc, copper, silver and stannous (e.g. zinc, copper and stannous chloride, and silver nitrate) may also be included.

Also contemplated according to the invention is the addition of compounds which can be used as fluoride source, dyes/colorants; preservatives, vitamins, pH-adjusting agents, anti-caries agents, desensitizing agents etc.

Enzymes

Other essential components used in oral care products and in oral care products of the invention are enzymes. Enzymes are biological catalysts of chemical reactions in living systems. Enzymes combine with the substrates on which they act forming an intermediate enzyme-substrate complex. This complex is then converted to a reaction product and a liberated enzyme which continue its specific enzymatic function.

Enzymes provide several benefits when used for cleansing of the oral cavity. Proteases break down salivary proteins, which are adsorbed onto the tooth surface and form the pellicle, the first layer of resulting plaque. Proteases along with lipases destroy bacteria by lysing proteins and lipids which form the structural components of bacterial cell walls and membranes. Dextranase breaks down the organic skeletal structure produced by bacteria that forms a matrix for bacterial adhesion. Proteases and amylases, not only prevents plague formation, but also prevents the development of calculus by breaking-up the carbohydrate-protein complex that binds calcium, preventing mineralization.

A toothpaste produced from an oral care composition of the invention (in weight % of the final toothpaste composition) may typically comprise the following ingredients:

| | |
|---|---|
| Abrasive material | 10 to 70% |
| Humectant | 0 to 80% |
| Thickener | 0.1 to 20% |
| Binder | 0.01 to 10% |
| Sweetener | 0.1% to 5% |
| Foaming agent | 0 to 15% |
| Whitener | 0 to 5% |
| Enzymes | 0.0001% to 20% |

In a specific embodiment of the invention the oral care product is toothpaste having a pH in the range from 6.0 to about 8.0 comprising

| | |
|---|---|
| a) 10% to 70% | Abrasive material |
| b) 0 to 80% | Humectant |
| c) 0.1 to 20% | Thickener |
| d) 0.01 to 10% | Binder |
| e) 0.1% to 5% | Sweetener |
| f) 0 to 15% | Foaming agent |
| g) 0 to 5% | Whitener |
| i) 0.0001% to 20% | Enzymes |

Said enzymes referred to under i) include a *Paecilomyces lilacinum* dextranase and mutanase described above, and optionally other types of enzymes mentioned above known to be used in toothpastes and the like.

A mouth wash produced from an oral care composition of the invention (in weight % of the final mouth wash composition) may typically comprise the following ingredients:

| | | |
|---|---|---|
| 0–20% | Humectant | |
| 0–2% | Surfactant | |
| 0–5% | Enzymes | |
| 0–20% | Ethanol | |
| 0–2% | Other ingredients (e.g. flavour, sweetener active ingredients such as fluorides) | |
| 0–70% | Water | |

The mouth wash composition may be buffered with an appropriate buffer e.g. sodium citrate or phosphate in the pH-range 6–8.

The mouth wash may be in none-diluted form (i.e. must be diluted before use).

Said enzymes referred include a *Paecilomyces lilacinum* dextranase and mutanase described above, and optionally other types of enzymes mentioned above known to be used in mouth washes.

Use of an Oral Care Composition or Product

In the third aspect the invention relates to the use of the composition of the invention or an oral care product of the invention for preventing the formation of plague or for removing dental plaque.

Using a product of the invention typically involves applying a safe and effective amount of said product to the oral cavity. These amounts (e.g. from 0.3 to about 2 grams), if it is a toothpaste or toothgel, is kept in the mount from about 15 seconds to about 12 hours.

Method of Manufacture

The oral care composition and products of the present invention can be made using methods which are common in the oral product area.

MATERIALS AND METHODS

Materials

Dextranase produced by *Paecilomyces lilacinum* (available from Novo Nordisk A/S).

Mutanase produced by *Trichoderma harzianum* CBS 243.71 (available from Novo Mordisk A/S)

Microorganisms

*Streptococcus mutans* strain CBS 350.71 identifiable as OMZ 176

Actinomyces viscosusDSM 42329

*Fusobacterium nucleatum* subsp. polymorphum DSM 20482

Solutions

Britton-Robinson Buffer

Erythrosin B (Sigma)

Equipment

Chromameter CR-200 (Minolta).

Preparation of Hydroxyapatite Disks

Hydroxyapatite disks are prepared by compressing 250 mg of hydroxyapatite in a disk die at about 5,900 kg (13,000 lbs) of pressure for 5 minutes. The disks are then sintered at 600° C. for 4 hours and finally hydrated with sterile de-ionised water.

Sterilisation of Hydroxyapatite Disks

HA disks are sterilised at 180° C. for two hours, hydrated with the sterilised de-ionised water and placed in a lid of Nunc tube (10 ml volume).

Mutan Preparation

Mutan is prepared by growing *Streptococcus mutans* CBS 350.71 at pH 6.5, 37° C. (kept constant), and with an aeration rate of 75 rpm in a medium comprised of the following components:

| | |
|---|---|
| NZ-Case | 6.5 g/liter |
| Yeast Extract | 6 g/liter |
| $(NH_4)_2SO_4$ | 20 g/liter |
| $K_2PO_4$ | 3 g/liter |
| Glucose | 50 g/liter |
| Pluronic PE6100 | 0.1% |

After 35 hours, sucrose is added to a final concentration of 60 g/liter to induce glucosyltransferase. The total fermentation time is 75 hours. The supernatant from the fermentation is centrifuged and filtered (sterile). Sucrose is then added to the supernatant to a final concentration of 5% (pH is adjusted to pH 7.0 with acetic acid) and the solution is stirred overnight at 37° C. The solution is filtered and the insoluble mutan is harvested on propex and washed extensively with deionized water containing 1% sodium benzoate, pH 5 (adjusted with acetic acid). Finally, the insoluble mutan is lyophilized and ground.

Determination of Dextranase Activity (KDU)

One Kilo Novo Dextranase Unit (1 KDU) is the amount of enzyme which breaks down dextran forming reducing sugar equivalent to 1 g maltose per hour in Novo Nordisk' method for determination of dextranase based on the following standard conditions:

| | |
|---|---|
| Substrate | Dextran 500 (Pharmacia) |
| Reaction time | 20 minutes |
| Temperature | 40° C. |
| pH | 5.4 |

A detailed description of Novo Nordisk's analytical method (AF 120) is available on request.

Determination of Mutanase Activity (MU)

One Mutanase Unit (MU) is the amount of enzyme which under standard conditions liberates 1 $\mu$mol reducing sugar (calculated as glucose) per minute.

Standard Conditions

| | |
|---|---|
| Substrate | 1.5% mutan |
| Reaction time | 15 minutes |
| Temperature | 40° C. |
| pH | 5.5 |

A detailed description of Novo Nordisk's analytical method (AF 180/1-GB) is available from Novo Nordisk A/S an request.

Preparation of Mutan Adhered Glass Wall

*Streptococcus mutans* OMZ 176 (CBS 350.71) is inoculated in a glass tube (22 mm diameter×150 mm height) containing 10 ml Todd Hewitt Broth with 2% sucrose and the tube is allowed to stand overnight at 37° C. The broth is discarded and adhered mutan and *Streptococcus mutans* cells on glass wall are washed twice with 10 ml of 0.85% NaCl solution.

Assessment of the Plague Removing Effect

The method used for assessing the plague removal effect is based on the method described by Kao in JP2250816. According to the present method the hydroxyapatite disks are coated with a biofilm comprising three strain of oral micro-organisms (*Streprtococcus mutans, Actinomyces viscosus* and *Fusobacterium nucleatum*).

To test plaque removing effect 0.1% Erythrosin B in PBS is used to stain plaque present on the hydroxyapatite disks red. The intensity of the red color (i.e. a*) is measured on a Chromameter CR-200. The max. a* value is 60. Values below that indicate a less intensive red color (i.e. less plaque present). If the a* value is determined to zero no red color is present (i.e. no plaque).

EXAMPLES

Example 1
Hydrolysis of Mutan at pHs from 5.0 to 8.0

Mutan prepared as described in the "Materials and Method" section was dispersed in deionized water with an ultrasonicater in a concentration of 16 mg/ml to prepare a substrate suspension.

*Paecilomyces lilacinum* mutanase and *Tricnoderma harzianum* CBS 243.71 dextranase dissolved in a 0.05 M acetate buffer were diluted with deionized water.
The following enzyme solutions were prepared:

Dextranase solution (4 KDU/ml),

Mutanase solution (4 MU/ml), and a mixed enzyme solution (4 KDU and 4 MU/ml).

Further, 50 mM Britton-Robinson buffer solutions having the pH adjusted to 5.0, 5.5, 6.0, 6.5, 7.0, 7.5 and 8.0 were also prepared.

Then 250 µl the above mentioned enzyme solutions and 500 µl of buffer solution were mixed in a microcentrifuge tube. Immediately thereafter 250 µl of the prepared Mutan suspension was added and incubated at 37° C. in a shaker at the maximum speed. After exactly 30 minutes, 250 µl of 0.5 N HCl was added to terminate the enzymatic reaction. Each of the reaction mixtures were subjected to centrifugation. The solubilized sugar, in the obtained supernatant, was determined according to the anthrone reaction method (J. H. Roe, (1955), J. Biol. Chem. 212, p. 335).

The result of the experiments are displayed in FIG. 1. As can be seen from FIG. 1 the combined use of the Dextranase and the Mutanase give a synergistic effect when hydrolysing mutan within pHs from 5.0 to 8.0.

Example 2
Hydrolysis of Mutan Adhered to Glass Walls at pH 7.0

To mimic dental plaque adhering on the teeth surface glass tubes wish adhered mutan were prepared as described above in the "MaterLal and Methods"-section.

The following Mutanase and Dextranase solutions, dissolved in a 0.05 M acetate buffer, were diluted with a 30 mM Britton-Robinson buffer (pH 7.0):

Dextranase solution (1 KDU/ml),

Mutanase solution (1 MU/ml), and a mixed Dextranase and Mutanase solution (1 KDU and 1 MU/ml).

5 ml of each of the above mentioned enzyme solutions, incubated at 37° C. for 15 minutes prior to the experiment was poured to a glass tube with the adhered mutan. The glass tubes were incubated at 37° C.

1000 µl of a 0 time control was taken out immediately and mixed with 500 µl of a 0.5 N HCl to stop the enzymatic reaction. At 5, 10, 15, 30 minutes, 1000 µl samples were taken out and immediately mixed with 500 µl of a 0.5 N HCl.

Each of the reaction mixture was subjected to centrifugation. The solubilized sugar in the obtained supernatant was determined in the same manner as Example 1.

Figure 2:
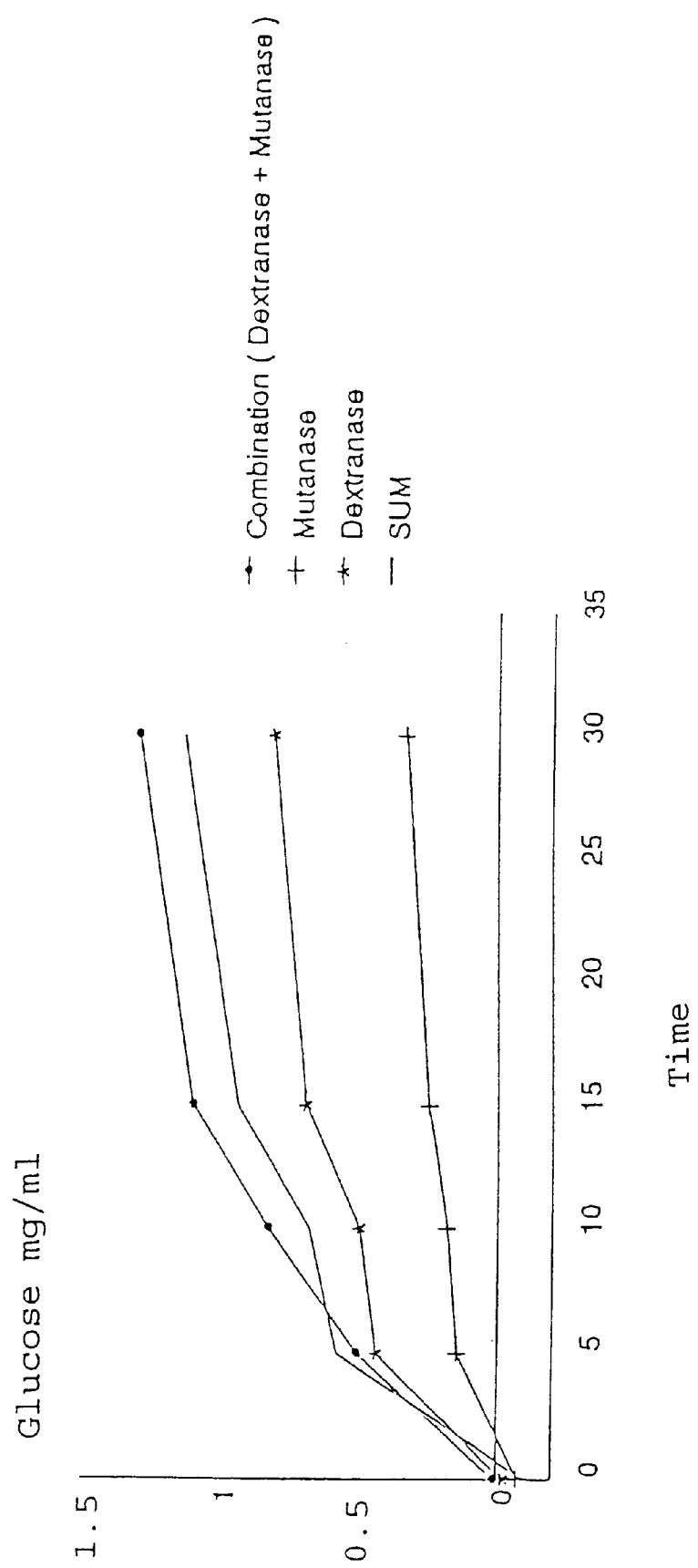
FIG. 2 shows plaque removal in an in vitro assay at pH 7

The result of the experiments are displayed in FIG. 2. As can be seen from FIG. 2 the combined use of the Dextranase and the Mutanase give a synergistic effect when hydrolysing mutan adhered on a glass wall at pH 7.0.

Example 3
Plague Removing Effect at pH 7.0

Three oral microorganisms, *Streprtococcus mutans Actinomyces viscosus* and *Fusobacterium nucleatum*, respectively, were cultivated anaerobically for three days at 37° C. Hydroxyapatite disks coated with sterilized saliva were immersed in a culture broth during cultivation so that oral biofilm was formed on a salivary coated hydroxyapatite disks. After cultivation, the disks were briefly rinsed with a phosphate buffered saline and then treated with the enzyme solution prepared in 40 mM Britton-Robinson buffer, pH 7.0, shown in a Table for 20 minutes at 37° C.

TABLE 1

| Treatment | Mutanase | Dextranase |
|---|---|---|
| 1 | 0 | 0 |
| 2 | 1 MU/ml | 0 |
| 3 | 0 | 1 kDU/ml |
| 4 | 1 MU/ml | 1 kDU/ml |

The disks were rinsed briefly with PBS and then incubated in a 1 ml 0.1% Erythrosin B in PBS for 1 minute to stains plaque present on the hydroxyapatite disks red. The disks were air dried overnight. The intensity of the red color (i.e. a*) was measured on a Chromameter CR-200. The higher the a* value is the more red are the hydroxyapatite disks. The Erythrosin B solution was removed and the disks were rinsed with PBS for a few minutes.

Figure 3:
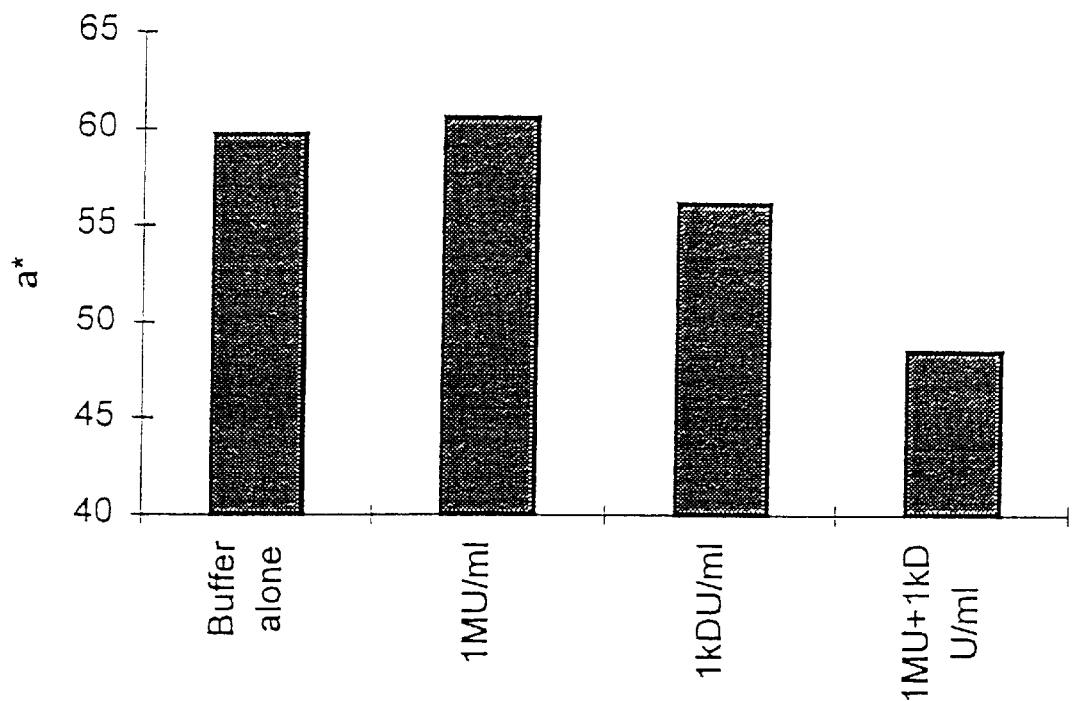
FIG. 3 shows the plaque removing effect of dextanase in combination with mutanase at pH 7.

The result of the test is shown in FIG. 3. As can be seen hydroxyapatite disk treated with 1 KDU/ml dextranase and 1 MU/ml mutanase removes plaque more efficiently than dextanase and mutanase separately. The combination of dextranase and mutanase has a synergistic effect on the plaque removal effect at pH 7.0.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. An oral care composition comprising a dextranase derived from *Paecilomyces lilacinum* and a mutanase derived from *Trichoderma harzianum*, wherein the composition has a pH ranging from 6.0 to 8.0.

2. The oral care composition according to claim 1, wherein the dextranase and mutanase are substantially active in the composition at temperatures between 20° C. and 40° C.

3. The oral care composition according to claim 1, further comprising one or more enzymes selected from the group consisting of a protease, endoglucosidase, lipase, and amylase.

4. An oral care product comprising the oral care composition of claim 1.

5. The oral care product according to claim 4, wherein said product is a dentrifice selected from the group consisting of a tootpase, a tooth powder, and a mouth wash.

* * * * *